United States Patent
Sakurai

(10) Patent No.: US 7,749,550 B2
(45) Date of Patent: Jul. 6, 2010

(54) FLUID KONJAK MATERIAL AND ITS PRODUCTION AND USE

(76) Inventor: Seiya Sakurai, 1367-20, Oaza Shimohideya, Okegawa-shi, Saitama 363-0025 (JP)

( * ) Notice: Subject to any disclaimer, the term of this patent is extended or adjusted under 35 U.S.C. 154(b) by 180 days.

(21) Appl. No.: 11/908,371

(22) PCT Filed: Jan. 10, 2007

(86) PCT No.: PCT/JP2007/050174

§ 371 (c)(1), (2), (4) Date: Sep. 11, 2007

(87) PCT Pub. No.: WO2007/080894

PCT Pub. Date: Jul. 19, 2007

(65) Prior Publication Data

US 2009/0028967 A1 Jan. 29, 2009

(30) Foreign Application Priority Data

Jan. 11, 2006 (JP) .............................. 2006-003773

(51) Int. Cl.
*A61K 36/00* (2006.01)
(52) U.S. Cl. ...................... 424/773; 424/725
(58) Field of Classification Search ........................ None
See application file for complete search history.

(56) References Cited

U.S. PATENT DOCUMENTS 3,973,008 A   8/1976   Sugiyama et al.
4,971,814 A * 11/1990 Tomita et al. .................. 426/52
5,422,133 A   6/1995   Yamamoto et al.
2003/0138545 A1* 7/2003 Sun ............................ 426/590

FOREIGN PATENT DOCUMENTS

| JP | 60-221054 |   | 11/1985 |
| JP | 05-199856 |   | 8/1993 |
| JP | 05-207854 |   | 8/1993 |
| JP | 06-007106 | * | 1/1994 |
| JP | 07-298842 | * | 11/1995 |
| JP | 07-313120 | * | 12/1995 |
| JP | 7-313120 |   | 12/1995 |
| JP | 08336375 A |   | 12/1996 |
| JP | 2001-333726 |   | 12/2001 |
| JP | 2002051710 A |   | 2/2002 |
| JP | 2002-335899 | * | 11/2002 |

OTHER PUBLICATIONS

Soo-Kyung et al., Rheological properties of konjac glucomannan dispersions, Korean Journal of Food Science and Technology, 27(2):246 (1995).

* cited by examiner

*Primary Examiner*—Christopher R. Tate
(74) *Attorney, Agent, or Firm*—Browdy and Neimark, PLLC

(57) ABSTRACT

A fluid konjak material, which can be mixed with any other edible material uniformly at a high concentration while sufficiently keeping the gelling power and the biological effect intrinsic to konjak mannan, is provided by swelling and dissolving konjak flour in water, treating the resultant with alkali at a pH of at least 10, lowering the pH to less than 8, heating the composition with forced stirring and enzymatically treating the forcedly-stirred composition.

14 Claims, No Drawings

FLUID KONJAK MATERIAL AND ITS PRODUCTION AND USE

TECHNICAL FIELD

The present invention relates to a fluid konjak material having a low viscosity though containing a large amount of konjak flour. The invention also relates to a method for producing the fluid konjak material having the characteristic, and to its use.

BACKGROUND ART

Konjak (devils' tongue) is a food widely and habitually taken by ordinary consumers for a long time, and it is eaten as it is alone or is taken as combined with any other edible material and cooked. With the recent diet boom, konjak has become specifically noted as a low-calorie health food, and konjak-containing foods prepared by adding konjak to various foods have been developed.

Konjak is generally produced by adding alkali such as calcium hydroxide to a paste prepared by grinding konjak corms or prepared by swelling konjak flour with water, thereby gelling it at a pH of from 10.5 to 12. Produced according to the process, konjak has a peculiar alkali smell, and because of it, the number of persons who dislike konjak is not small. Even if persons try taking a large amount of konjak for diet or health maintenance, it may be often impossible as they may soon be surfeited with konjak owing to its alkali smell and simple taste.

Accordingly, various trials are made of mixing konjak with favorable edibles or dispersing it in favorable drinks thereby processing it into more readily eatable or drinkable products and providing them to consumers.

For example, an improved konjak paste is proposed, which is produced by finely cutting alkali-added konjak jelly so as to be readily mixed with any other edible or drinkable (Patent Reference 1). Another method is also proposed, comprising mixing a pure water-soluble konjak mannan, which is prepared by purifying the water-soluble konjak mannan contained in konjak flour, with any other edible or drinkable (Patent Reference 2). Still another method is proposed, comprising enzymatically treating the konjak mannan contained in konjak flour to give a liquid product (Patent Reference 3).

Patent Reference 1: JP-A 5-207854
Patent Reference 2: JP-B 54-20582
Patent Reference 3: JP-A 5-199856

DISCLOSURE OF THE INVENTION

Problems Solved by the Invention

However, the cut matter in the paste in Patent Reference 1 is the alkali-gelled konjak itself, and such cut matter could not uniformly mix with any other edible or drinkable to a satisfactory degree. Accordingly, even though the paste of Patent Reference 1 is used, it is still impossible to produce foods and drinks having a higher konjak concentration than the concentration of ordinary konjak. In addition, the problem of alkali smell still remains unsolved, and therefore, even though the paste is used, it is impossible to produce foods and drinks with which a large amount of konjak can be taken.

The water-soluble konjak mannan in Patent Reference 2 is swellable to the same degree as that of konjak flour, and therefore there is naturally a limitation in increasing its concentration while it is kept fluid. Konjak flour may be mixed with water and swollen to give a paste, whereupon, however, a fluid material that contains konjak flour at a concentration much larger than 3% by weight could not be produced. Accordingly, even though the pure water-soluble konjak mannan is used, it is still impossible to provide a fluid material having a high concentration and capable of being readily mixed with any other edible material and to provide drinks that contain konjak flour at a high concentration.

Further, the liquid matter of Patent Reference 3 is prepared by enzymatically treating konjak flour until it becomes liquid without being gelled under an alkaline condition, in which, therefore, the starting konjak mannan may be much degraded to low-molecular substances and may have greatly lost its gelling powder and biological effect intrinsic to konjak mannan. Accordingly, this does not meet with its intrinsic object to attain diet and health maintenance.

Taking the prior art problems into consideration, we, the present inventors have assiduously studied for the purpose of providing a composition in which a konjak material may be mixed with any other edible material at a high concentration while fully keeping the gelling power and the biological effect intrinsic to konjak mannan. In addition, we have further studied for the purpose of providing foods and drinks capable of more effectively promoting diet and health maintenance.

Means for Solving the Problems

As a result, we have found that the objects can be attained by the invention having the following constitutions.

EMBODIMENT 1

A fluid konjak material having a konjak flour content of at least 3.5% by weight, having a viscosity at 20° C. of at most 4 Pa·s and having a gelling power.

EMBODIMENT 2

The fluid konjak material of embodiment 1, which has a konjak flour content of at least 5% by weight.

EMBODIMENT 3

A method for producing a fluid konjak material of embodiment 1 or 2, which comprises:

swelling and dissolving konjak flour in water and treating it with alkali at a pH of at least 9 to give an alkali composition (Step A), lowering the pH of the alkali composition to less than 8 and heating it with forced stirring to give a forcedly-stirred composition (Step B), enzymatically treating the forcedly-stirred composition (Step C).

EMBODIMENT 4

The method for producing a fluid konjak material of embodiment 3, wherein in the step B, the pH of the alkali composition is lowered to 5 to 7.

EMBODIMENT 5

The method for producing a fluid konjak material of embodiment 4 or 5, wherein the pH reduction in the step B is attained by addition of at least one compound selected from the group consisting of lactic acid, citric acid, acetic acid, succinic acid, tartaric acid, gluconic acid and malic acid.

EMBODIMENT 6

The method for producing a fluid konjak material of any one of embodiments 3 to 5, wherein the enzymatic treatment in the step C is attained with at least one enzyme selected from the group consisting of cellulase, hemicellulase, pectinase, protease and galactomannase.

EMBODIMENT 7

The method for producing a fluid konjak material of any one of embodiments 3 to 6, wherein the enzymatically-treated composition obtained in the step C is further subjected to cutting the massive grains in the enzymatically-treated composition (Step D).

EMBODIMENT 8

The method for producing a fluid konjak material of embodiment 7, wherein the cutting treatment in the step D is attained by the use of a rotary food cutter or a homogenizer.

EMBODIMENT 9

A method for producing a drink, comprising mixing the fluid konjak material of embodiment 1 or 2 with a drink component.

EMBODIMENT 10

A method for producing a food, comprising mixing the fluid konjak material of embodiment 1 or 2 with an edible material.

EMBODIMENT 11

A drink containing the fluid konjak material of embodiment 1 or 2.

EMBODIMENT 12

A food containing the fluid konjak material of embodiment 1 or 2.

EMBODIMENT 13

A composition for depressing blood cholesterol comprising the fluid konjak material of embodiment 1 or 2.

EMBODIMENT 14

A composition for depressing body fat comprising the fluid konjak material of embodiment 1 or 2.

ADVANTAGEOUS EFFECT OF THE INVENTION

The fluid konjak material of the invention may be uniformly mixed with any other edible material at a high concentration while keeping the gelling power and the biological effect intrinsic to konjak mannan. Accordingly, the fluid konjak material of the invention may provide foods and drinks containing a konjak material uniformly and at a high concentration. In addition, the fluid konjak material of the invention has an effect of depressing a high blood cholesterol level and an effect of depressing a high body fat level.

BEST MODE FOR CARRYING OUT THE INVENTION

The invention is described in detail hereinunder. The description of the constitutive elements of the invention given hereinunder is for some typical embodiments of the invention, to which, however, the invention should not be limited. In this description, the numerical range expressed by the wording "a number to another number" means the range that falls between the former number indicating the lowermost limit of the range and the latter number indicating the uppermost limit thereof.

The fluid konjak material of the invention is characterized by having a konjak flour content of at least 3.5% by weight and having a viscosity at 20° C. of at most 4 Pa·s.

The konjak flour content of the fluid konjak material of the invention is more preferably at least 4% by weight, even more preferably at least 4.5% by weight, still more preferably at least 5% by weight, further more preferably at least 5.5% by weight. The uppermost limit of the content is not specifically defined. For example, a fluid konjak material having a konjak flour content of 8% by weight may be produced.

The viscosity at 20° C. of the fluid konjak material of the invention is more preferably at most 3.5 Pa·s, even more preferably at most 3 Pa·s, still more preferably at most 2.8 Pa·s. Its lowermost limit is preferably at least 0.1 Pa·s, more preferably at least 0.2 Pa·s, even more preferably at least 0.3 Pa·s, still more preferably at least 0.4 Pa·s. When defined in point of the range thereof, the viscosity at 20° C. of the fluid konjak material of the invention is preferably from 0.1 to 4 Pa·s, more preferably from 0.1 to 3.5 Pa·s, still more preferably from 0.2 to 3.2 Pa·s, further more preferably from 0.3 to 3 Pa·s, still further more preferably from 0.4 to 2.8 Pa·s.

The fluid konjak material of the invention has a gelling power. The wording "has a gelling power" as referred to herein means that the material may exhibit a function of gelling when heated under an alkaline condition.

No one has heretofore produced a fluid konjak material that has a low viscosity and has a gelling power though containing a large amount of konjak flour, like the fluid konjak material of the invention. Konjak flour is swollen with water to give a paste. However, the swelling degree intrinsic to konjak flour is limited, and naturally, therefore, a fluid material containing konjak flour in an amount much larger than 3% by weight could not be obtained. For obtaining a fluid material that contains a large amount of konjak flour, a method may be taken into consideration which comprises degrading the konjak mannan (glucomannan) that constitutes konjak flour to such a degree that its swellability may considerably lower, and then dissolving or dispersing it in water. However, the method is unfavorable since the composition obtained according to it could not keep the gelling power and the biological effect intrinsic to konjak mannan. The present inventors have assiduously studied for a method of increasing the concentration of a fluid konjak material while keeping the gelling power and the biological effect intrinsic to konjak mannan and, as a result, have found that, according to the production method of the invention, a fluid konjak material satisfying the above-mentioned conditions may be produced in a simplified manner.

The production method for a fluid konjak material of the invention comprises the following steps A to D. Of the steps A to D, the steps A to C are indispensable steps, and the step D is an optional step that is preferably carried out.

(Step A) a step of swelling and dissolving konjak flour in water and treating it with alkali at a pH of at least 9 to give an alkali composition, (Step B) a step of lowering the pH of the alkali composition to less than 8 and heating it with forced stirring to give a forcedly-stirred composition, (Step C) a step of enzymatically treating the forcedly-stirred composition, (step D) a step of cutting the massive grains in the enzymatically-treated composition.

The step A is a step of obtaining an alkali composition with partially utilizing the gelling power of konjak flour. In a conventional method of konjak production, gelled konjak is obtained with almost completely utilizing the gelling power of konjak flour; but in the step A of the present invention, utilization of the gelling power of konjak flour is retarded. (Specifically, when konjak flour is stirred with water added thereto, and the konjak gellation is stopped in the state that it has become pasty.) The gellation is thus controlled in that condition, whereby the finally obtained fluid konjak material may still keep its gelling power, and when this is mixed with any other edible material or drink component, then the mixture may exhibit the gelling power.

The konjak flour to be used in the step A is not specifically defined in point of its home and kind. Konjak corms may be powdered directly as they are; or the konjak flour may be purified. In addition, it is not always necessary that the grains of the konjak flour are uniform.

The alkali to be added to the konjak flour in the step A may be suitably selected from those usable in foods. Konjak flour may gel generally under an alkali condition at pH of at least 9. Accordingly, the amount of the alkali to be added to the konjak flour in the step A may be suitably controlled so that the pH could fall within the range. In a preferred embodiment, a basic amino acid, a basic salt or a mixture of the two is added as the alkali.

As the basic amino acid, generally used are arginine, histidine, lysine, citrulline and ornithine, either singly or as combined. Arginine and lysine are especially preferred. Preferably, the basic amino acid is added in an amount of from 1.25 to 20% by weight of konjak flour. The basic amino acid has a high pH-buffering capability. Accordingly, another advantage of using the basic amino acid is that it gives a stable pH level and provides tasty foods and drinks of stable quality.

As the basic substance, generally used are organic acid salts such as sodium citrate, sodium tartrate, sodium malate, sodium acetate, sodium lactate, sodium succinate; phosphates such as sodium polyphosphate, sodium pyrophosphate, sodium metaphosphate, disodium phosphate, trisodium phosphate, potassium polyphosphate, potassium pyrophosphate, potassium metaphosphate, dipotassium phosphate, tripotassium phosphate; carbonates such as sodium carbonate, sodium hydrogencarbonate, potassium carbonate, calcium carbonate, magnesium carbonate; sulfates such as potassium sulfate, sodium sulfate, calcium sulfate, magnesium sulfate; sodium hydroxide and potassium hydroxide, either singly or as combined. Any and every basic salt for foods may be used as the basic salt in the invention.

Various acids or acidic salts may be combined for making the combinations have a buffering effect, and the combinations finally having a pH to fall within an alkali range may be used herein. As the acids and the basic salts in the case, usable are citric acid, tartaric acid, malic acid, acetic acid, lactic acid, phosphoric acid, monosodium phosphate, monopotassium malate. Preferably, the amount to be used is from 0.01 to 20% by weight of konjak flour.

When a basic amino acid and a basic salt are combined and used, then the functions of the two may be well balanced, thereby facilitating the intended production. Specifically, a basic amino acid has a high pH buffering capability and may give a stable pH, but on the contrary, its drawback is that, when it is used, the pH of the mixture is difficult to control at a desired level. On the other hand, a basic salt has a low pH buffering capability, but its advantage is that, when it is used for a selected substance, then the pH of the mixture is easy to control at a desired level. Accordingly, when the two are well combined, then the intended pH control may be easy and a uniform alkali composition may be produced with retarding the pH fluctuation depending on the starting material and water used.

The pH is controlled to be at least 9, but preferably from 9.0 to 10.5, more preferably from 9.3 to 10.2. When the pH is at least 9.0, then the mixture may be efficiently gelled. On the other hand, when the pH is at most 10.5, then a trouble of too much gellation to cause water release or alkali smell formation may be readily prevented.

The order of adding water and alkali to konjak flour is not specifically defined. For example, water may be first added to konjak flour so as to swell and dissolve it; and then an alkali may be added to and mixed and reacted with it; or water to which an alkali has been added may be added to konjak flour whereby the konjak flour may be swollen and reacted at the same time. Alternatively, an alkali may be first added to konjak flour, and then water may be added thereto to swell and dissolve it. These methods may be suitably combined. Further, water that contains a basic amino acid may be first added to konjak flour, and then water that contains a basic salt may be added thereto. Any of these methods is employable as the process of the step A so far as swelling with water and reaction with alkali may go on therein.

One preferred example is as follows: First, water is added to konjak flour to swell and dissolve it, then a basic acid, a basic salt or a mixture of the two is added to the obtained konjak paste, and well mixed. Another preferred example is as follows: A basic amino acid, a basic salt or a mixture of the two is mixed and dissolved in water, and konjak flour is swollen and dissolved in the resulting solution. Still another preferred example is as follows: A basic amino acid, a basic salt or a mixture of the two is previously mixed with konjak flour, and then water is added to and mixed with it to swell and dissolve it.

The amount of water to be added is preferably from 10 to 27 parts by weight, more preferably from 11 to 23 parts by weight, even more preferably from 12 to 20 parts by weight, still more preferably from 13 to 18 parts by weight, relative to 1 part by weight of konjak flour.

After water and alkali have been added to konjak flour, it is desirable that they are well reacted at room temperature or under heat. For example, they may be treated at room temperature for 2 to 4 hours or at 60° C. for 15 minutes to 1 hour or so, whereby they may be well reacted. The condition of the temperature and the time may be suitably determined, depending on the ratio of konjak flour and alkali, the method of adding them, the pH and the type of the food or drink as the final product. In general, when the pH is high, then the reaction time may be short; and when the pH is low, then the reaction time is preferably long.

In the step A, any other food component and additive than the above may be added to the system, not too much detracting from the effect of the invention. For example, emulsifier, starch, oil, fat, seasoning or flavoring and the like may be suitably added. Its type and amount may be determined depending on the type of the intended food, the production condition and the storage environment for it. Such food component and additive may be added in the subsequent steps (for example, in the step B, the step C and/or the step D).

Next, the step B is described.

The step B is a step of lowering the pH of the alkali composition obtained in the step A to less than 8 and heating it with forced stirring. The composition obtained in the step A is highly viscous, and, as it is, therefore, it could not be well mixed with any other edible material or drink component. In the step B of the invention, the alkali composition is forcedly stirred, though it is not easy to stir it at room temperature.

The forced stirring in the step B is such that a stirring unit introduced into the alkali composition is rotated at 30 rpm or more against the viscosity of the alkali composition, or the composition is stirred to the same degree. The stirring unit includes a rotary shaft equipped with from 2 to 12 blades. While forcedly stirred in that manner, the system is gradually heated. The temperature elevation range is preferably from 5 to 60° C., more preferably from 10 to 55° C., even more preferably from 20 to 50° C. The heating profile is preferably such that the heating speed is slow first and then gradually increased. The ultimate temperature is preferably from 40 to 75° C., more preferably from 50 to 70° C. In the step B, it is desirable that the stirring speed is elevated along with the temperature elevation. Preferably, the stirring speed is elevated finally by at least 1.5 times, more preferably at least 1.8 times, even more preferably at least 2 times. Concretely, in one preferred embodiment, the temperature is elevated from room temperature up to 60° C. and the revolution speed is increased from 30 rpm to 60 rpm. Preferably, the stirring time is from 2 to 45 minutes, more preferably from 3 to 30 minutes, even more preferably from 5 to 20 minutes.

Before or during the temperature elevation, acid is added to the system so as to lower the pH of the system to less than 8. Not specifically defined in point of its type, the acid to be added may be any one not too much detracting from the effect of the invention. In general, an organic acid solution of lactic acid, acetic acid, citric acid, succinic acid, malic acid, tartaric acid, gluconic acid or the like may be added. The acid may be added all at a time, or may be continuously or intermittently added. Preferably, the pH is controlled to be from 4.6 to 7.5, more preferably from 5 to 7. In particular, it is desirable that, not taking a treatment of first controlling the pH to a pH range of less than 4.6, especially less than 5 and then increasing the pH, the system is directly controlled to have a pH value falling within the intended pH range, in view of the effect of the material taken in bodies, the taste and the miscibility of the material.

Next described is the step C.

The step C is a step of enzymatically treating the forcedly-stirred composition obtained in the step B. The enzyme to be used for the enzymatic treatment is preferably one or more enzymes selected from cellulose, hemicellulase, pectinase, protease and galactomannase. These enzymes may be commercially-available ones. For example, Sankyo's Sucrase N may be preferably used.

The enzymatic treatment is effected at a temperature at which the enzyme is fully active. In general, it may be attained under heat, preferably at 40 to 75° C., more preferably at 50 to 70° C. The treating time may vary depending on the type of the enzyme and the temperature, but may be generally from 10 minutes to 12 hours, preferably from 20 minutes to 6 hours, more preferably from 30 minutes to 3 hours. During the enzymatic treatment, the system is preferably stirred.

After the enzymatic treatment, it is desirable that the enzyme is deactivated. The method of enzyme deactivation is not specifically defined, not having any excessive negative influences on the effect of the invention. For example, the object may be attained when the system is heated up to a temperature at which the enzyme could be deactivated. In case where the above-mentioned Sucrase N is used, for example, the system may be heated up to 90° C. to deactivate the enzyme.

Next described is the step D.

The step D is a step of cutting the massive grains in the enzymatically-treated composition obtained in the step C. In the step C, a fluid konjak material satisfying the viscosity condition of the invention may be obtained. In case where the viscosity of the composition obtained in the step C is desired to be lower, or in case where the massive grains in the composition obtained in the step C are desired to be made smaller, then the step D is preferably carried out. The viscosity may be further lowered by from 0.2 to 1 Pa·s or so.

The cutting in the step D is preferably effected with a homogenizer or a food cutter. The details of the structure of the food cutter and the homogenizer are not specifically defined. In case where the enzymatically-treated composition obtained in the step C contains massive grains, the massive grains may be mechanically cut, for which a high-speed rotary cutter or a high-performance homogenizer may be preferably used. The mechanical cutting treatment may be repeated plural times. As a result of the cutting treatment, the fluid konjak material may have further improved dispersibility and may be more uniformly mixed with any other edible material and drink component.

The fluid konjak material of the invention is not limited to those produced according to the production method of the invention, but irrespective of the production method for them, any ones satisfying the claimed condition are within the scope of the fluid konjak material of the invention. For example, the operation in each step of the production method of the invention may be suitably modified, added or deleted so as to produce products that are technically equivalent to each other.

Though containing a high concentration of konjak flour, the fluid konjak material of the invention may still have a gelling power even though having a low viscosity. Accordingly, it may be readily and more uniformly mixed with any other edible material and drink component. Therefore, when the fluid konjak material of the invention is used, foods and drinks containing a konjak material at a high concentration may be efficiently produced in a simplified manner. In particular, the industrial value of the invention is extremely high in that, according to the invention, high-concentration konjak drinks may be produced that could not be produced when a conventional konjak material is used. Specifically, great patience is needed in taking a large amount of konjak produced from konjak flour, but the drink of the invention produced from the same amount of konjak may be readily and deliciously drunk; and therefore, the drink is helpful for easy diet and health maintenance.

The form of the food to be produced by the use of the fluid konjak material of the invention is not specifically defined.

According to the invention, various foods containing konjak material may be produced. For example, soba (buckwheat noodle), noodle, deep-fried food, hamburger pate, wiener, fish paste such as hampen (cake of pounded fish), as well as jelly, potage, ice cream, butter, yogurt, mayonnaise, ketchup, dressing, source of barbecued chicken or kabayaki (split and broiled eel), dressing may be produced.

The food provided by the use of the invention has a good texture well tightened as a whole. Accordingly, free water is difficult to move in the food, and when the food contains broth infiltrated thereinto, then its power to retain the broth therein is extremely high. In addition, the food hardly collapses and its shape retentiveness is good. Specifically, it does not expand like rubber, and on the contrary, it does not shrink. In addition, the food of the invention may well absorb and keep seasonings. Accordingly, when the food is used in stewed dishes, then it may well absorb and keep the taste of the broth used and may be a delicious food. In addition, those who have eaten the food may enjoy a soft and juicy taste of the food as a whole.

The form of the drink to be produced by the use of the fluid konjak material of the invention is not also specifically defined. Typically, the drink include juices. When the fluid konjak material of the invention is used, then a full-bodied and refreshing-feel drink may be provided. Except for juices, the invention may also apply to cocoa, milk, fermented milk, functional flavor drinks, etc.

Further, the alkali smell intrinsic to konjak is removed from the food and the drink of the invention, and therefore the food and the drink may be widely accepted by consumers. In particular, konjak itself may be produced according to the invention, and in this case, the alkali smell may be effectively masked and konjak with no offensive smell may be obtained though it is produced by heating under a strong alkali condition like conventionally.

When taken into bodies, the fluid konjak material of the invention exhibits a blood cholesterol level-depressing effect and a body fat level-depressing effect. Accordingly, the fluid konjak material of the invention is useful also as medicines. The fluid konjak material of the invention is produced from konjak flour eaten for a long time, and therefore it is well known that its safety is high. Since the highest concentration of the fluid konjak material of the invention is limited, it may be considered that even though the material is taken directly as it is, it may not overstep a pharmaceutically-acceptable amount. Depending on patients, however, the amount of the material to be given to them may be controlled individually.

In case where the fluid konjak material of the invention is processed into medicines, it may be formed into oral preparations according to a technique well known to those skilled in the art. A pharmaceutically-acceptable vehicle may be suitably selected and its necessary amount may be used in processing the material into pharmaceutical preparations.

EXAMPLES

The characteristics of the invention are described more concretely with reference to the following Examples and Comparative Examples. In the following Examples, the material used, its amount and the ratio, the details of the treatment and the treatment process may be suitably modified or changed not overstepping the spirit and the scope of the invention. Accordingly, the invention should not be limitatively interpreted by the Examples mentioned below.

Example 1

Production of Konjak Material (1) Preparation of Alkali Composition:

60 kg of purified konjak flour and 2.15 kg of sodium carbonate were added to and mixed with 1000 liters of water at 60° C., and reacted for 30 minutes to obtain an alkali composition [1] having a pH of 9.3.

Apart from it, 60 kg of purified konjak flour and 2.15 kg of sodium carbonate were added to and mixed with 1000 liters of water at 20° C., and reacted for 3 hours to obtain an alkali composition [2] having a pH of 9.3.

(2) pH Control:

An aqueous solution comprising citric acid and water in a ratio as in Table 1 was added to each alkali composition obtained in (1) and forcedly stirred at room temperature. The forced stirring was started by rotating a stirring unit (rotary shaft with 10 blades) inserted into a batch filled with each mixture, at room temperature at 30 rpm, and then the revolution speed was increased up to 60 rpm with the elevation of the temperature up to 60° C. From the alkali composition [1], prepared were pH-controlled compositions [1-a] to [1-i]; and from the alkali composition [2], prepared were pH-controlled compositions [2-a] to [2-i] The pH of each composition thus obtained is shown in Table 1.

TABLE 1

| Composition Number | 1-a<br>2-a | 1-b<br>2-b | 1-c<br>2-c | 1-d<br>2-d | 1-e<br>2-e | 1-f<br>2-f | 1-g<br>2-g | 1-h<br>2-h | 1-i<br>2-i |
|---|---|---|---|---|---|---|---|---|---|
| Amount of Citric Acid Added (kg) | 1 | 2 | 3 | 4 | 5 | 6 | 7 | 8 | 9 |
| Amount of Water Added (kg) | 100 | 100 | 100 | 100 | 100 | 100 | 100 | 100 | 100 |
| pH of Composition | 7.3 | 6.2 | 5.6 | 5.3 | 5.0 | 4.6 | 4.4 | 4.3 | 4.2 |

(3) Enzymatic Treatment:

0.05 parts by weight of "Sucrase N" (by Sankyo), an enzyme essentially comprising pectinase was added to 100 parts by weight of the pH-controlled composition obtained in (2), and the composition was thus enzymatically-treated at 60° C. for 2 hours. Next, this was heated up to 90° C. to deactivate the enzyme, and then cooled to room temperature, thereby obtaining enzymatically-treated compositions [1-a] to [1-i] and enzymatically-treated compositions [2-a] to [2-i].

(4) Cutting Treatment:

The massive grains in each enzymatically-treated composition obtained in (3) were pulverized with a foot cutter. As a result, pulverized compositions [1-a] to [1-i] and pulverized compositions [2-a] to [2-i] of good flowability were obtained. The viscosity of the compositions, as measured at 20° C. with a 50 Hz B-type viscometer, was within a range of from 2600 cp to 2800 cp (converted into a range of from 2.6 Pa·s to 2.8 Pa·s). The thus-obtained pulverized compositions had a gelling power under an alkali condition.

The fluid konjak material characterized by having a konjak flour content of at least 3.5% by weight and a viscosity at 20° C. of at most 4 Pa·s and having a gelling power could not be obtained when the stirring speed after the addition of the aqueous citric acid solution was changed to 10 rpm or when the system was first heated up to 60° C. and then the aqueous citric acid was added thereto.

In case where the amount of the purified konjak flour in (1) was changed to 40 kg, 45 kg, 50 kg, 55 kg or 80 kg and the above steps (1) to (4) were carried out, fluid konjak materials having 460 cp, 1400 cp, 2520 cp, 2600 cp and 3000 cp, respectively, and having a gelling power (having a converted value of 0.46 Pa·s, 1.4 Pa·s, 2.52 Pa·s, 2.6 Pa·s, and 3.0 Pa·s, respectively) were obtained.

Example 2

Production of Drink

Using the pulverized compositions [1-a] to [1-i] and the pulverized compositions [2-a] to [2-i] produced in Example 1, the materials were mixed as in Table 2 to produce drinks. In Table 2, the fluid konjak material corresponds to the pulverized composition.

The obtained drinks are all drinkable. In particular, those produced by using the pulverized compositions [1-a] to [1-f] and the pulverized compositions [2-a] to [2-f] were excellent as they did not almost smell. Among them, those produced by using the pulverized compositions [1-a] to [1-e] and the pulverized compositions [2-a] to [2-e] were more excellent.

When the pulverized compositions [1-a] to [1-f] and the pulverized compositions [2-a] to [2-f] were used, another advantage was confirmed that the drinks were easy to flavor. In particular, the drinks produced by using the pulverized compositions [1-a] to [1-e] and the pulverized compositions [2-a] to [2-e] were more excellent as they were easier to flavor.

The above tendency was the same also when drinks of the same formulation were produced by using the enzymatically-treated compositions [1-a] to [1-i] and the enzymatically-treated compositions [2-a] to [2-i].

TABLE 2

| Ingredient | wt. % |
| --- | --- |
| Fluid Konjak Material | 25 |
| Concentrated Carrot Juice | 3 |
| Sugar | 4 |
| Transparent Lemon Juice | 0.1 |
| Fructoligosaccharide | 1.5 |
| Trehalose | 1 |
| Citric Acid | 0.3 |
| Water | balance |
| Total | 100 |

Example 3

Production of Food

Using each of the pulverized compositions [1-a] to [1-i] and [2-a] to [2-i], and the enzymatically-treated compositions [1-a] to [1-i] and [2-a] to [2-i] as a fluid konjak material, the following foods were produced.

150 g of minced beef and 500 g of the fluid konjak material were well mixed and shaped to prepare meat pate. The meat pate was cooked. As compared with a cooked food of minced beef alone, the cooked food of the meat pate was juicy. The meat pate was once frozen and stored, and the thawed, and it was cooked in the same manner as above. The cooked foot was also juicy.

Example 4

Production of Another Food

Using each of the pulverized compositions [1-a] to [1-i] and [2-a] to [2-i], and the enzymatically-treated compositions [1-a] to [1-i] and [2-a] to [2-i] as a fluid konjak material, source of barbecued chicken was produced according to the following process.

400 g of the fluid konjak material, 180 ml of soy sauce, 80 g of sugar, 60 ml of vinegar, 2 g of synthetic seasoning, and 80 ml of water were well mixed with suitably heating to produce source. As compared with source produced not using the fluid konjak material, the thus-produced source had suitable viscosity and had plenty of body; and when applied to barbecued chicken, it was excellent not dropping down.

Example 5

Production of Preparation

The pulverized composition [1-c] of Example 1 was diluted 3 times with water and fully stirred and mixed to produce an oral preparation.

Test Example

The pulverized composition [1-c] of Example 1 was orally administered to a 10-week age fat male rat (Zucker fa/fa, Japan Medical Science Animal Material Laboratory), once a day for continuous 7 days. The dose corresponds to 80 mg/kg-body weight/day of konjak flour (×1 administration group) or 800 mg/kg-body weight/day of konjak flour (×10 administration group). Each group consists of 5 rats in the test. Two hours after the last administration on the day 7, the rats were sacrificed by cutting their head, and the blood was collected from them. According to the items of an ordinary human blood chemical test, the rat blood was analyzed for the total protein concentration in plasma, the blood glucose concentration (blood glucose level), total lipid, the neutral fat (triglyceride, TG), free fatty acid (FAA), total cholesterol, HDL-cholesterol, LDL-cholesterol, ester-type cholesterol, GOT and GPT. The abdomen of each rat was cut open, and the fat mass at the back was taken out and its weight was measured, thereby determining the weight of the fat accumulated in the abdomen.

As compared with that in the control group (145.8±4.03 mg/dl), the neutral fat decreased in the ×1 administration group (160.0±10.18 mg/dl) and in the ×10 administration group (155.4±14.92 mg/dl). The body fat amount also decreased, as compared with that in the control group (6.68±0.297 g), in the ×1 administration group (6.31±0.333 g) and further more in the ×10 administration group (6.18±0.191 g). As compared with that in the control group (5.6±0.53 mg/dl), the LDL-cholesterol also decreased in the ×1 administration group (5.2±0.49 mg/dl) and in the ×10 administration group (4.8±0.37 mg/dl). As compared with that in the control group (402.2±40.26 $\mu E_Q/l$), the free fatty acid significantly ($p<0.02$, $p<0.05$) increased in the ×1 administration group (554.4±27.97 $\mu E_Q/l$) and in the ×10 administration group (590.6±63.88 $\mu E_Q/l$), which confirms promoted fat combustion in the body to prevent fat accumulation therein. Regarding the body weight, there was found no difference between the control group (401±4.02 g), the ×1 administration group (406.5±4.49 g) and the ×10 administration group (392.4±1.42), which confirms that the administration of the fluid konjak material of the invention has no influence on the body weight.

The above results indicate that the fluid konjak material of the invention has a blood cholesterol level-depressing effect and a body fat level-depressing effect, and when it is taken, obesity may be prevented.

INDUSTRIAL APPLICABILITY

The fluid konjak material of the invention may be mixed with any other edible material uniformly at a high concentration, while sufficiently keeping the gelling power and the biological effect intrinsic to konjak mannan. Accordingly, the fluid konjak material of the invention may provide foods and drinks that contain a konjak material more uniformly at a high concentration. Therefore, the present invention has high applicability to the field of foods and drinks. In addition, the fluid konjak material of the invention has an effect of depressing a high blood cholesterol level and an effect of depressing a high body fat level. Therefore, the invention has high applicability to the field of medicine.

What is claimed is:

1. A method for producing a fluid konjak material having a gelling power, in which the fluid konjak material has a konjak flour content of at least 3.5% by weight and a viscosity at 20° C. of at most 4 Pa·s, which comprises:

swelling and dissolving konjak flour in water and treating the resultant with alkali at a pH of at least 9 to give an alkali composition, lowering the pH of the alkali composition to less than 8, and heating the composition with forced stirring to give a forcedly-stirred composition, and enzymatically treating the forcedly-stirred composition.

2. The method for producing a fluid konjak material according to claim 1, wherein the pH of the alkali composition is lowered to 5 to 7.

3. The method for producing a fluid konjak material according to claim 1, wherein the pH of the alkali composition is lowered by addition of at least one compound selected from the group consisting of lactic acid, citric acid, acetic acid, succinic acid, tartaric acid, gluconic acid and malic acid.

4. The method for producing a fluid konjak material according to claim 1, wherein the forcedly-stirred composition is enzymatically treated with at least one enzyme selected from the group consisting of cellulase, hemicellulase, pectinase, protease and galactomannase.

5. The method for producing a fluid konjak material according to claim 1, which further comprising cutting massive grains in the enzymatically-treated composition.

6. The method for producing a fluid konjak material according to claim 5, wherein the massive grains are cut by the use of a rotary food cutter or a homogenizer.

7. The method for producing a fluid konjak material according to claim 2, wherein the pH of the alkali composition is lowered by addition of at least one compound selected from the group consisting of lactic acid, citric acid, acetic acid, succinic acid, tartaric acid, gluconic acid and malic acid.

8. The method for producing a fluid konjak material according to claim 7, wherein the forcedly-stirred composition is enzymatically treated with at least one enzyme selected from the group consisting of cellulase, hemicellulase, pectinase, protease and galactomannase.

9. The method for producing a fluid konjak material according to claim 2, wherein the forcedly-stirred composition is enzymatically treated with at least one enzyme selected from the group consisting of cellulase, hemicellulase, pectinase, protease and galactomannase.

10. The method for producing a fluid konjak material according to claim 3, wherein the forcedly-stirred composition is enzymatically treated with at least one enzyme selected from the group consisting of cellulase, hemicellulase, pectinase, protease and galactomannase.

11. The method of claim 1 wherein the heating of the composition with forced stirring to give a forcedly stirred composition comprises stirring at a rate of at least 30 rpm and gradually heating during the stirring to raise the temperature of the composition at least 20° C. over time to reach a temperature of 40-75° C., and increasing the stirring speed during the heating by at least 1.5×, the stirring being conducted for 2-45 minutes.

12. A fluid konjak material having a gelling power, which has a konjak flour content of at least 3.5% by weight and a viscosity at 20° C. of at most 4 Pa·s, made by the method of claim 1.

13. A fluid konjak material having a gelling power, which has a konjak flour content of at least 5% by weight and a viscosity at 20° C. of at most 4 Pa·s, made by the method of claim 11.

14. A method for producing a drink or food, which comprises mixing the fluid konjak material of claim 12 with a drink or food component.

* * * * *